United States Patent [19]

Nakamura et al.

[11] Patent Number: 4,950,468
[45] Date of Patent: Aug. 21, 1990

[54] HAIR TREATING COMPOSITION

[75] Inventors: Takanari Nakamura, Takatsuki; Hiroshi Nishimura, Kyoto; Makoto Tada, Takatsuki, all of Japan

[73] Assignee: Sunstar Kabushiki Kaisha, Osaka, Japan

[21] Appl. No.: 241,843

[22] Filed: Sep. 8, 1988

[51] Int. Cl.$^5$ .................. A61K 7/075; A61K 7/08
[52] U.S. Cl. .................................. 424/70; 424/71; 424/78; 424/47
[58] Field of Search .............. 424/70, 71, 78, 47

[56] References Cited

U.S. PATENT DOCUMENTS 4,728,457 3/1988 Fieler et al. .................... 252/547 X

FOREIGN PATENT DOCUMENTS

| 4709 | 1/1983 | Japan .................................. 424/70 |
| 59204 | 3/1987 | Japan . |
| 222109 | 9/1988 | Japan . |
| 2170216 | 7/1986 | United Kingdom .................. 424/70 |
| 2188655 | 10/1987 | United Kingdom .............. 8/127.51 |
| 2192194 | 1/1988 | United Kingdom . |
| 2196980 | 5/1988 | United Kingdom . |

*Primary Examiner*—Ellis P. Robinson
*Assistant Examiner*—Susan S. Rucker
*Attorney, Agent, or Firm*—Wegner & Bretschneider

[57] ABSTRACT

A hair treating composition having excellent resistance to washing which comprises a dimethyl silicone rubber and a quaternary ammonium salt ingredient consisting of stearyltrimethylammonium chloride and behenyltrimethylammonium chloride.

1 Claim, No Drawings

HAIR TREATING COMPOSITION

FIELD OF THE INVENTION

The present invention relates to a hair treating composition. More particularly, it relates to a hair treating composition having excellent resistance to washing which comprises a dimethyl silicone rubber and a specific quaternary ammonium salt ingredient.

BACKGROUND OF THE INVENTION

Various hair treating compositions such as a hair treatment preparation, a hair rinse, etc. have been used to provide gloss and elasticity to hair, or to take care of injured hair. For example, a hair treating composition in which a quaternary ammonium salt is formulated to provide softness to hair is known. By using such a hair treating composition, the quaternary ammonium salt itself is adsorbed on hair and thereby softness and antistat effect are provided to hair. Further, for improving gloss and conditioning, a hair care product having water resistance in which a silicone rubber is formulated has been proposed (XIVth IFSCC Congress Barcelona 1986, Vol 1, 455–459).

However, a hair treating composition using a quaternary ammonium salt has insufficient adsorptivity on hair because its adsorption on hair is based on mere affinity between hair and the quaternary ammonium salt. That is, although a hair treating composition using a quaternary ammonium salt can stand against swimming, sweat, etc., it is washed out by washing operation with a shampoo or the like. Therefore, its adsorptivity is insufficient.

On the other hand, the above hair care product which uses a silicone rubber as well as a skin care composition having water resistance and permanence properties in which a dimethyl silicone rubber is formulated (see Japanese Patent Laid Open Publication No. 229810/1986) are also stand against swimming, sweat or the like. However, like a hair treating composition in which a quaternary ammonium salt is formulated, they are readily washed out by washing operation with a shampoo or the like.

In Japanese Patent Laid Open Publication No. 183517/1988, there is disclosed a hear treating composition containing a dimethyl silicone rubber and one of quaternary ammonium salts, behenyltrimethylammonium chloride, which provides improved gloss and smoothness to hair. However, there is no teaching or suggestion about resistance to strong washing operation.

It has been found that a hair treating composition comprising a dimethyl silicone rubber and a specific combination of quaternary ammonium salts shows excellent resistance to strong washing operation with a shampoo or the like.

OBJECTS OF THE INVENTION

The main object of the present invention is to provide a hair treating composition having resistance to strong washing operation with a shampoo or the like (resistance to washing) hair treatment function of which is hardly deteriorated.

This object as well as other objects and advantages of the present invention will become apparent to those skilled in the art from the following description.

SUMMARY OF THE INVENTION

According to the present invention, there is provided a hair treating composition comprises
(a) 0.05 to 2.5% by weight of a dimethyl silicone rubber of the formula [I] as described hereinafter, and
(b) 0.1 to 5.0% by weight of a quaternary ammonium salt ingredient consisting of stearyltrimethylammonium chloride and behenyltrimethylammonium chloride,
the weight ratio of said dimethyl silicone rubber: said quaternary ammonium salt ingredient being 1:2 to 1:10.

In the hair treating composition of the present invention, adsorpability of the dimethyl silicone rubber and the quaternary ammonium salt ingredient to hair becomes significantly strong due to the specific combination thereof and they can not be readily desorbed from hair even by washing. Therefore, the hair treating composition of the present invention shows an increased residual effect in comparison with a conventional hair treating composition to show excellent treatment effect and resistance to washing.

DETAILED DESCRIPTION OF THE INVENTION

The dimethyl silicone rubber used in the hair treating composition of the present invention is represented by the following formula [I]:

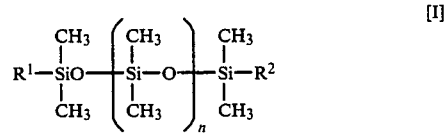

wherein which $R^1$ and $R^2$ are methyl or hydroxy; and n is an integer of 4000 to 9000.

Representative examples of dimethyl silicone rubber of the formula [I] include Toshiba Silicone TSE-200 ($R^1$ and $R^2$ are hydroxy and n is 5500 to 9000) and TSE-200A ($R^1$ and $R^2$ are methyl and n is 5500 to 9000) manufactured by Toshiba Silicone Co., Ltd., Japan and the like, and one or more of them can be formulated in the hair treating composition of the present invention in an amount of 0.05 to 2.5% by weight based on the total weight of the composition. When the amount is less than 0.05% by weight, the effect for providing softness, smoothness and gloss to hair becomes insufficient. When the amount is more than 2.5% by weight, it is necessary to formulate a lager amount of the quaternary ammonium salt ingredient, which results in a problem of safety such as irritation of the skin and the like.

The quaternary ammonium salt ingredient of the hair treating composition of the present invention is stearyltrimethylammonium chloride and behenyltrimethylammonium chloride. They can be formulated in the hair treating composition of the present invention in an amount of 0.1 to 5.0% by weight based on the total weight of the composition. When the amount of the quaternary ammonium salt ingredient is less than 0.1% by weight, resistance to washing of the composition becomes insufficient and, when the amount is more than 5.0% by weight, a problem such as too strong irritation to the skin is caused.

Preferably, the weight ratio of stearyltrimethylammonium chloride: behenyltrimethylammonium chloride is preferably 9:1 to 1:9. When the amount of stearyltrimethylammonium chloride is too large, desired feeling to be provided by behenyltrimethylammonium chloride is not expected. On the other hand, when the amount of stearyltrimethylammonium chloride is to small, desired softness to be provided is not expected.

In the hair treating composition of the present invention, the weight ratio of the dimethyl silicone rubber: the quaternary ammonium salt ingredient is 1:2 to 1:10. When the amount of the quaternary ammonium salt ingredient is too small, water resistance becomes insufficient. On the other hand, when the amount of the quaternary ammonium salt ingredient is too large, the composition becomes sticky and properties provided by the dimethyl silicone rubber such as smoothness are impaired.

The hair treating composition of the present invention can be prepared in the form of a hair treatment preparation, a hair rinse, a hair treatment spray, a treatment pack and the like according to a conventional method.

Furthermore, oily ingredients (e.g., liquid paraffin, triglyceride, ester oil, wax, etc.), coloring agents, perfumery, pH adjustors (e.g., phosphoric acid, citric acid, etc.), humectants (e.g., pyrrolidone carboxylate, lactic acid, etc.) and the like can be formulated in the hair treating composition of the present invention in so far as they do not deteriorate the properties of the composition.

Particularly, it is preferred to formulate the dimethyl silicone rubber by dissolving it in a volatile silicone or a isoparaffinic hydrocarbon having a boiling point of 150° to 350° C. The volatile silicone includes a linear silicone of the formula:

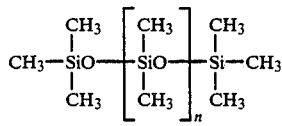

wherein n is an integer of 0 to 5, and a cyclic silicone of the formula:

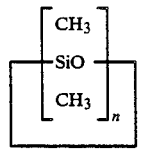

wherein n is an integer of 3 to 7. Examples of the isoparaffinic hydrocarbon include NISSEKI ISOSOL 300 (b.p. 170° to 189° C.), NISSEKI ISOSOL 400 (b.p. 206° to 257° C.), ISOLAN P (b.p. 264° to 318° C.) and ISO-LAN R (b.p. 272° to 342° C.), ISOLAN S (b.p. 282° to 350° C.) manufactured by Nippon Sekiyu Kagaku Co., Ltd., Japan as well as ISOPAR G (b.p. 156° to 175° C.), ISOPAR H (b.p. 176° to 192° C.), ISOPAR L (b.p. 188° to 210° C.) and ISOPAR M (b.p. 204° to 254° C.) manufactured by Exxon Chemicals, U.S.A.

In the hair treating composition of the present invention, adsorptivity of the dimethyl silicone rubber and the quaternary ammonium salt ingredient to hair becomes remarkably strong by incorporating these ingredients. Therefore, they are not washed out with a shampoo, etc. and provide softness and antistat effect to hair.

The following Examples and Comparative Examples further illustrate the present invention in detail but are not to be construed to limit the scope thereof.

EXAMPLES 1 to 12 AND COMPARATIVE EXAMPLES 1 to 8

According to the formulations as shown in Table 1A, each hair treatment preparation was prepared by incorporating the dimethyl silicone rubber and stearyltrimethylammonium chloride and/or behenyltrimethylammonium chloride by heating the oil phase to 70° to 80° C., adding the oil phase to the aqueous phase other than the perfume at 70° to 80° C., cooling the mixture and adding the perfume. Resistance to washing of the resulting hair treatment preparation was evaluated as follows.

Test for Evaluating Resistance to Washing (1) A bundle of intact human hair (5 g, 20 cm in length) was dipped in the hair treatment preparation (100 g) for three seconds and then the preparation was rinsed out with warm water.

(2) Then, the bundle was air-dried and washed with 10 ml of 1% aqueous sodium lauryl sulfate solution. Thereafter, it was rinsed out thoroughly with hot water and air-dried again. One cycle of this operation was counted as one washing.

Evaluation

Evaluation of a sample was carried out according to the follow methods.

(1) Gloss

Gloss was evaluated under white light using white light powder device (Ushio Co., Ltd., Japan) by organoleptic test involving five professional panells.

(2) Softness and feeling

Softness and feeling were evaluated by organoleptic test involving five professional panelists.

(3) Easy combing

The bundle of human hair was treated with the above mentioned treatment preparation, washed and dried. Thereafter, a comb equipped with push-pull gage (Imada Seisakusho Co., Ltd., Japan) was pulled through the bundle of human hair to measure the maximum stress applied to the gage.

Evaluation Criteria

| Score | Evaluation |
|---|---|
| Gloss, Softness and feeling: | |
| 5 | almost the same conditions as those immediately after treatment with the hair treatment preparation |
| 4 | slightly inferior in comparison with the conditions immediately after treatment with the preparation |
| 3 | somewhat inferior in comparison with the conditions immediately after treatment with the preparation |
| 2 | considerably inferior in comparison with the conditions immediately after treatment with the preparation |
| 1 | clearly inferior in comparison with the conditions immediately after treatment the preparation |
| Easy combing: | |
| Score | Evaluation |
| 4 | less than 30 g |
| 3 | not less than 30 g but less than 100 g |
| 2 | not less than 100 g but less than 200 g |
| 1 | not less than 200 g |

|   | Overall evaluation: |   | C | the score 2 is present in the above evaluation |
|---|---|---|---|---|
| A | each score of the above evaluation is 4 or 5 |   | D | the score 1 is present in the above evaluation |
| B | the score 3 is present in the above evaluation |   |   |   |

TABLE 1A

| Ingredients | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Oil phase | | | | | | | | | | |
| Dimethylsilicone rubber | 0.5 | 0.5 | 0.5 | 0.05 | 0.5 | 1.0 | 2.0 | 1.0 | 1.0 | 1.0 |
| Cyclic silicone | 5.0 | 5.0 | 5.0 | 5.0 | 5.0 | 5.0 | 5.0 | 5.0 | 5.0 | 5.0 |
| Stearyltrimethyl-ammonium chloride | 0.5 | 1.5 | 2.5 | 0.1 | 1.0 | 2.0 | 2.0 | 0.3 | 0.9 | 1.5 |
| Behenyltrimethyl-ammonium chloride | 0.5 | 1.5 | 2.5 | 0.1 | 1.0 | 2.0 | 2.0 | 2.7 | 2.1 | 1.5 |
| Self-emulsifiable glyceryl monostearate | 1.0 | 1.0 | 1.0 | 1.0 | 1.0 | 1.0 | 1.0 | 1.0 | 1.0 | 1.0 |
| Ethylene glycol monostearate | 1.0 | 1.0 | 1.0 | 1.0 | 1.0 | 1.0 | 1.0 | 1.0 | 1.0 | 1.0 |
| Cetyl alcohol | 0.5 | 0.5 | 0.5 | 0.5 | 0.5 | 0.5 | 0.5 | 0.5 | 0.5 | 0.5 |
| Lanolin alcohol | 0.5 | 0.5 | 0.5 | 0.5 | 0.5 | 0.5 | 0.5 | 0.5 | 0.5 | 0.5 |
| Aqueous phase | | | | | | | | | | |
| Glycerin | 2.0 | 2.0 | 2.0 | 2.0 | 2.0 | 2.0 | 2.0 | 2.0 | 2.0 | 2.0 |
| Preservative | q.s. | q.s. | q.s. | q.s. | q.s. | q.s. | q.s. | q.s. | q.s. | q.s. |
| Perfume/coloring agent | q.s. | q.s. | q.s. | q.s. | q.s. | q.s. | q.s. | q.s. | q.s. | q.s. |
| Distilled water | | | | | up to 100 | | | | | |

(% by weight)

| Ingredients | Ex. 11 | Ex. 12 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|---|---|
| Oil phase | | | | | | | | | | |
| Dimethylsilicone rubber | 1.0 | 1.0 | 0.5 | 0.5 | 0.02 | 3.0 | 1.0 | 1.0 | 1.0 | 1.0 |
| Cyclic silicone | 5.0 | 5.0 | 5.0 | 5.0 | 5.0 | 5.0 | 5.0 | 5.0 | 5.0 | 5.0 |
| Stearyltrimethyl-ammonium chloride | 0.25 | 2.7 | 0.25 | 3.0 | 0.04 | 5.0 | 0.2 | 2.8 | — | 3.0 |
| Behenyltrimethyl-ammonium chloride | 0.25 | 0.3 | 0.25 | 3.0 | 0.04 | 5.0 | 2.8 | 0.2 | 3.0 | — |
| Self-emulsifiable glyceryl monostearate | 1.0 | 1.0 | 1.0 | 1.0 | 1.0 | 1.0 | 1.0 | 1.0 | 1.0 | 1.0 |
| Ethylene glycol monostearate | 1.0 | 1.0 | 1.0 | 1.0 | 1.0 | 1.0 | 1.0 | 1.0 | 1.0 | 1.0 |
| Cetyl alcohol | 0.5 | 0.5 | 0.5 | 0.5 | 0.5 | 0.5 | 0.5 | 0.5 | 0.5 | 0.5 |
| Lanolin alcohol | 0.5 | 0.5 | 0.5 | 0.5 | 0.5 | 0.5 | 0.5 | 0.5 | 0.5 | 0.5 |
| Aqueous phase | | | | | | | | | | |
| Glycerin | 2.0 | 2.0 | 2.0 | 2.0 | 2.0 | 2.0 | 2.0 | 2.0 | 2.0 | 2.0 |
| Preservative | q.s. | q.s. | q.s. | q.s. | q.s. | q.s. | q.s. | q.s. | q.s. | q.s. |
| Perfume/coloring agent | q.s. | q.s. | q.s. | q.s. | q.s. | q.s. | q.s. | q.s. | q.s. | q.s. |
| Distilled water | | | | | up to 100 | | | | | |

TABLE 1B (% by weight)

| | Score | | | | | | | | | |
|---|---|---|---|---|---|---|---|---|---|---|
| Evaluation | Ex. 1 | Ex. 2 | Ex. 3 | Ex. 4 | Ex. 5 | Ex. 6 | Ex. 7 | Ex. 8 | Ex. 9 | Ex. 10 |
| Gloss after 5 washing cycles | 4 | 4 | 5 | 4 | 4 | 5 | 4 | 4 | 5 | 5 |
| Softness after 5 washing cycles | 4 | 5 | 5 | 4 | 5 | 5 | 4 | 4 | 4 | 5 |
| Feeling after 5 washing cycles | 4 | 5 | 5 | 4 | 4 | 5 | 4 | 5 | 5 | 5 |
| Easy combing after 5 washing cycles | 4 | 4 | 4 | 4 | 4 | 5 | 4 | 5 | 5 | 5 |
| Overall evaluation | A | A | A | A | A | A | A | A | A | A |

| | Score | | | | | | | | | |
|---|---|---|---|---|---|---|---|---|---|---|
| Evaluation | Ex. 11 | Ex. 12 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
| Gloss after 5 washing cycles | 5 | 5 | 4 | 3 | 2 | 5 | 3 | 4 | 4 | 4 |
| Softness after 5 washing cycles | 5 | 5 | 2 | 4 | 2 | 5 | 3 | 5 | 3 | 4 |
| Feeling after 5 washing cycles | 4 | 4 | 2 | 4 | 2 | 5 | 4 | 3 | 4 | 3 |
| Easy combing after 5 washing cycles | 5 | 4 | 4 | 2 | 1 | 5 | 4 | 4 | 4 | 4 |

TABLE 1B-continued

| Overall evaluation | A | A | C | C | D | A* | B | B | B | B |

Note
*There is a problem on safety such as irritation of the skin.

EXAMPLE 13

Hair Treatment Preparation

According to the following formulation, a hair treatment preparation was prepared by a conventional method.

| Ingredients | % by weight |
|---|---|
| Oil phase | |
| Dimethyl silicone rubber | 1.0 |
| Cyclic silicone | 5.0 |
| Stearyltrimethylammonium chloride | 2.0 |
| Behenyltrimethylammonium chloride | 0.5 |
| Self-emulsifiable glyceryl monostearate | 1.5 |
| Ethylene glycol monostearate | 1.0 |
| Stearic acid | 0.5 |
| Olive oil | 1 0 |
| Aqueous phase | |
| Preservative | q.s. |
| Coloring agent | q.s. |
| Methyl cellulose | 0.5 |
| Distilled water | up to 100 |
| Perfume | q.s. |

The mixture of the oil phase was heated to 70° to 80° C. and the mixture was added to the mixture of the aqueous phase at 70° to 80° C. The perfume was added to the mixture with cooling to obtain the desired hair treatment preparation.

EXAMPLE 14

Hair Rinse

According to the following formulation, a hair rinse was prepared by a conventional method.

| Ingredients | % by weight |
|---|---|
| Oil phase | |
| Dimethyl silicone rubber | 0.5 |
| Cyclic silicone | 5.0 |
| Stearyltrimethylammonium chloride | 1.5 |
| Behenyltrimethylammonium chloride | 0.8 |
| Lipophilic glyceryl monostearate | 1.0 |
| Sorbitol monooleate | 0.3 |
| Oleic acid | 0.1 |
| Aqueous phase | |
| Preservative | q.s |
| Coloring agent | q.s. |
| Carboxymethylcellulose | 0.8 |
| Distilled water | up to 100 |
| Perfume | q.s |

The mixture of the oil phase was heated to 70° to 80° C. and the mixture was added to the mixture of the aqueous phase at 70° to 80° C. The perfume was added to the mixture with cooling to obtain the desired hair rinse.

EXAMPLE 15

Hair Treatment Spray

| Ingredients | % by weight |
|---|---|
| Dimethyl silicone rubber | 0.25 |
| Cyclic silicone | 0.1 |
| Stearytrimethyl-ammonium chloride | 0.5 |
| Behenyltrimethyl-ammonium chloride | 0.1 |
| Propellant flon 11/flon 12 (50/50) | 99.05 |

The ingredients other than propellant were filled in a can and then the propellant was filled to obtain the desired hair treatment spray.

EXAMPLE 16

Aerosol Foam-Type Hair Treatment Preparation

| Ingredients | % by weight |
|---|---|
| Oil phase | |
| Dimethyl silicone rubber | 1.0 |
| Polyether modified silicone | 4.0 |
| Gafquat 755 (manufactured by Gaf Co.) | 1.0 |
| Lauryldimethylamine oxide | 0.5 |
| Stearyltrimethylammonium chloride | 1.5 |
| Behenyltrimethylammonium chloride | 0.5 |
| Cyclic silicone | 4.0 |
| Aqueous phase | |
| Propylene glycol | 5.0 |
| Preservative | q.s. |
| Distilled water | up to 100 |

The oil phase was heated to 70° to 80° C. and mixed with the aqueous phase at 70° to 80° C. to obtain a stock solution. 92 parts by weight of the stock solution and 8 parts by weight of LPG as the propellant were packed in a container to prepare the desired aerosol product.

What is claimed is:

1. A hair treating composition comprising:
   (a) 0.05 to 2.5% by weight of a dimethyl silicone rubber of the formula:

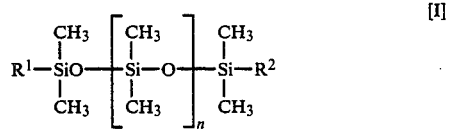

[I]

wherein $R^1$ and $R^2$ are methyl or hydroxy; and n is an integer of 4000 to 9000, and
   (b) 0.1 to 5.0% by weight of a quaternary ammonium salt ingredient consisting of stearyltrimethylammonium chloride and behenyltrimethylammonium chloride, the weight ratio of said dimethyl silicone rubber: said quaternary ammonium salt ingredient being from 1:2 to 1:10 and wherein the weight ratio of stearyltrimethylammonium chloride: behenyltrimethylammonium chloride is from 9:1 to 1:9.

* * * * *